(12) United States Patent
Vadgama et al.

(10) Patent No.: US 6,300,123 B1
(45) Date of Patent: Oct. 9, 2001

(54) SENSOR EMPLOYING IMPEDANCE MEASUREMENTS

(75) Inventors: Pankaj M. Vadgama, Worsley; Keith S. R. Warriner, Long Eaton, both of (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/297,124

(22) PCT Filed: Oct. 22, 1997

(86) PCT No.: PCT/GB97/02777

§ 371 Date: Jul. 19, 1999

§ 102(e) Date: Jul. 19, 1999

(87) PCT Pub. No.: WO98/19153

PCT Pub. Date: May 7, 1998

(30) Foreign Application Priority Data

Oct. 26, 1996 (GB) .................................... 9622304

(51) Int. Cl.⁷ ............................... C12M 1/40; C12Q 1/00
(52) U.S. Cl. ..................................... 435/287.1; 435/287.2; 435/287.9; 435/817; 435/4; 422/82.02; 436/151; 436/537
(58) Field of Search ................. 435/287.9, 817, 435/287.2, 287.1, 4, 26; 204/403; 422/82.01, 82.02; 436/537, 151, 149

(56) References Cited

U.S. PATENT DOCUMENTS

| | | |
|---|---|---|
| 4,444,892 | 4/1984 | Malmros . |
| 5,250,439 * | 10/1993 | Musho et al. ........................... 435/25 |
| 5,766,934 * | 6/1998 | Guiseppi-Elie .................... 435/287.9 |
| 6,083,366 * | 7/2000 | Higson ................................ 204/403 |

FOREIGN PATENT DOCUMENTS

| | | |
|---|---|---|
| 0 193 154 | 9/1986 | (EP) . |
| 0 251 915 | 1/1988 | (EP) . |
| 0 314 009 | 5/1989 | (EP) . |
| 0 402 917 | 12/1990 | (EP) . |
| 0 467 219 | 1/1992 | (EP) . |
| 2 229 005 | 12/1990 | (GB) . |
| 88/09808 | 12/1988 | (WO) . |
| 93/06237 | 4/1993 | (WO) . |
| 94/28414 | 12/1994 | (WO) . |
| 96/33403 * | 10/1996 | (WO) . |

OTHER PUBLICATIONS

Souteyrand et al: "Direct Detection of Biomolecules by Electrochemical Impedance Measurements" Sensors and Actuators B, vol. B20, No. 1, pp. 63–69, XP000455277, May 1994.

Lyons et al: "Poly (Pyrrole) Based Amperometric Sensors: Theory and Characterization" Analyst XP002055101, Apr. 1993.

* cited by examiner

Primary Examiner—William H. Beisner
(74) Attorney, Agent, or Firm—Nixon & Vanderhye P.C.

(57) ABSTRACT

A sensor uses an immobilized affinity component capable of interacting with analyte species and being associated with a conducting polymer such that the interaction of the affinity component and the analyte induces change in the electrical properties of the polymer. An AC signal is applied to the polymer, and the induced change in impedance resulting from the interaction is measured. The impedance is measured at a frequency or frequencies corresponding to a peak or peaks in the relationship between frequency and impedance change for the polymer and the analyte. The measurement may be made by reference to the imaginary or real component of impedance. The polymer may be in the form of a layer bridging two electrodes between which the impedance is measured. The two electrodes may together define an interdigitated electrode assembly.

18 Claims, 7 Drawing Sheets

SENSOR EMPLOYING IMPEDANCE MEASUREMENTS

BACKGROUND OF THE INVENTION

1. Field of the Invention

The present invention relates to a sensor and more particularly but not exclusively, to a biosensor.

2. Related Art

Biosensors are used for determining the presence and/or amount of an analyte in a sample. Typically a biosensor comprises a bio-component (e.g. enzyme) which is specific for the analyte to be determined and which interacts therewith to produce a detectable change indicative of the presence and/or amount of the analyte in a sample. A particular example of biosensor comprises an enzyme electrode system whereby the catalytic reaction of suitable redox enzyme on analyte produces an electroactive species which is detected electrochemically. A glucose sensor using glucose oxidase as the bio-component is a specific example of an enzyme electrode system. Here glucose is oxidised by oxygen via glucose oxidase to produce gluconic acid and hydrogen peroxide. the latter being detected electrochemically. Systems based on oxidase enzymes are particularly well suited to biosensors because the oxygen acts as the mediator (i.e. to shuttle electrons to the electrode from the enzyme active site) and no additional reagents are required (i.e. it is a reagentless system). However, not all analytes have corresponding oxidase enzymes therefore limiting the number of substrates that can be determined using this system. Dehydrogenase enzymes are more diverse than oxidases and hence enable that a wider variety of analytes can be measured by biosensor systems. A key disadvantage of dehydrogenase enzymes, however, is that oxygen cannot act as a mediating (electron accepting) species and instead soluble nicatinamide adenine dinucleotide $(NAD(P)^+/NAD(P)H)$ cofactors are required to act as electron acceptors/donors. Thus, biosensor systems based on dehydrogenase enzymes are not reagentless which restricts practical application.

It is known from European Patent Specification No. 402917 to provide a biosensor employing a thin surfactant polymeric electrically conducting layer to which may be bound members of specific binding pairs. Binding of an analyte to the specific binding pair member layer changes the electrical properties of the layer to enable the detection of the analyte. A DC voltage is applied between a pair of electrodes bridged by the layer, and changes in the voltage are measured. Alternatively, electrical alternating current measurements may be used for filtering out background noise due to non-specific matrix effects. Unfortunately, the sensitivity of such biosensors is limited as the measured changes in the electrical properties of the layer are relatively small.

SUMMARY OF THE INVENTION

The object of the present invention is to obviate or mitigate the abovementioned disadvantage.

According to the present invention there is provided a sensor comprising an immobilised affinity component capable of interacting with an analyte species and being associated with a conducting polymer such that the interaction of the affinity component and the analyte induces a change in the electrical properties of the polymer, means for applying an AC signal to the polymer, and means for detecting the response of the polymer to the applied signal to detect the induced change, wherein the detecting means comprises means for measuring the impedance of the polymer at a frequency corresponding to a peak in the relationship between frequency and impedance change for the polymer and the analyte.

DETAILED DESCRIPTION OF EXEMPLARY EMBODIMENTS.

The present invention is based on the realisation that impedance changes are very frequency dependent and therefore sensitivity may be greatly enhanced by measuring the impedance to AC signals at a frequency or frequencies at which the change in impedance resulting from exposure to the analyte peaks.

The sensor of the present invention employs a conducting polymer to amplify, and transduce, the interaction between analyte and immobilised affinity component. During analyte interaction with the affinity component the electrochemical properties of the conducting polymer are altered and the changes detected, by measurement of impedance changes. Thus the interaction of the analyte species is directly transduced into a measurable signal with no need for formation of an electroactive product as in the case of conventional enzyme electrodes. The identity of the affinity component and the analyte species of interest and the structure of the conducting polymers, will determine the nature of the change in electrical properties which will result from the presence of the analyte. If the change is for example primarily capacitive, the imaginary component of the measured impedance is likely to exhibit a peak at a predetermined frequency and accordingly the imaginary component of the impedance should be monitored at that predetermined frequency. Conversely, if the change is primarily resistive, it may be more appropriate to monitor the real component of the impedance.

Conducting polymers are organic semi-conducting materials which can be reversibly switched through conducting and insulating states by varying the degree of oxidation, protonation and polymer chain orientation. In the sensor of the invention it is the interaction of the analyte with the affinity component which. we believe, alters the local electrostatic interactions between polymer and immobilised affinity component inducing changes in polymer orientation (hence electrical properties i.e. charge mobility).

The affinity component will preferably be a macromolecule.

Preferably the sensor of the invention is a biosensor so that the affinity component is a biocomponent. for example an enzyme, such as kinase or dehydrogenase, or L(+) lactic dehydrogenase suitable for measuring pyruvate. Alternatively the affinity component may be an antibody, antigen, lectin or receptor.

The polymer may be in the form of a layer bridging two electrodes between which the impedance is measured. The two electrodes may together define an interdigitated electrode assembly. The polymer layer may have a thickness of less than 5 $\mu$m, and may contain or incorporate a layer of, immobilised binding agent. The affinity component may be entrapped within a gel layer provided oil the conducting polymer layer on the side thereof remote from the electrodes, the gel thickness being less than 50 $\mu$m. Alternatively, the affinity component may be immobilised within the conducting polymer.

The conducting polymer may be poly(3-methylthiophene) or poly(pyrrole).

Thus, in one embodiment the affinity molecule is an enzyme whereby subtle changes in electrostatic potential of the protein structure during analyte interaction induces changes in the local environment in contact with the polymer film which may be detected through measuring the impedance of the supporting conducting polymer.

Enzymes which can be used as the affinity component arc those that require two or more components to achieve enzyme catalytic activity. That is to observe the interaction of analyte with enzyme no catalytic activity should occur and the enzyme should merely act as an affinity site (i.e. analogous to antibody and antigen interaction). For example. dehydrogenase enzymes arc a specific enzyme class that may find utility in the described sensors whereby in the absence of soluble $NAD(P)^+/NAD(P)H$ cofactor the interaction of substrate (analyte) with the affinity site of the enzyme is measured. Dehydrogenases for lactate, pyruvate, citrate and malate are possible examples of enzymes which may be used. A further class of enzyme are kinases where both the analyte and phosphate donating ATP are required to permit catalytic activity. An example is with hexokiniase which catalyses the phosphorylation of glucose by ATP. In the absence of glucose the interaction of ATP with hexokinase immobilised over a conducting polymer film induces a change in polymer conductivity. The use of other enzymes such as oxidases lipases, hydratases and proteinases may be restricted as these systems do not require the addition of dual substrates. For example with oxidases the addition of analyte will furness the catalytic activity of the enzyme unless oxygen is totally excluded. In such circumstances the enzyme is acting catalytically and not as an affinity site which leads to exclusion in the described sensor format. Oxidases, however may be used if the FAD prosthetic group (responsible for electron transfer from substrate to oxygen) is removed (apo-enzyme). Under such circumstances the enzyme now acts as an affinity site for substrate due to its inability to interact with molecular oxygen.

If the affinity molecules are antibodies, antigens lectins and receptors rather than enzymes, the interaction between analyte and affinity sites can be detected directly unlike the multi-step protocols requiring indicator labels (e.g. radioisotope, enzyme conjugate) currently used in standard analysis. Antibodies can be used to detect small molecules such as pesticides (e.g,. dinitropentol derivatives), antiepipeptic (phenytoin) and restricted drugs (e.g. morphine, heroin). Alternatively, the target may be protein (albumin) or hormone (leutenisinig hormone). Lectin substrates can be sugar residues, for example, Concanavilin A for glucose/dextrin binding.

Antigens may also be immobilised to act is the affinity component in the detection of the corresponding antibody or receptor. For example, leutenising hormone could be immobilised and used to detect anti-leutenising hormone in solution. Low molecular weight antigens (e.g. drugs) may be used as affinity molecules provided that covalent linkage of the molecule to the surface of the conducting polymer is undertaken. This will provide accessibility to allow anitibody/receptor interaction and in addition assure retention of the affinity molecule.

Studies so far have indicated that the conducting polymer type has an influence over detection of analyte interaction with immobilised affinity molecule. For example work using L(+) lactic dehydrogenase has indicated that poly(3-methylthiophene) (as opposed to poly(pyrrole) and poly(aniline)) is suitable for detecting interaction of pyruvate analyte with immobilised L(+) lactic dehydrogenase. In a further example, interaction of leuteinising hormone with immobilised antibody (anti-leuteinising hormone) can be detected when poly(pyrrole) is the supporting conducting polymer.

The reasons for the apparent different sensitivities of conducting polymer films are at this time unclear. However, it must be noted that the properties of conducting polymers do differ. For example, poly(3-methylthiophene) has a more ordered and flexible structure compared to that of poly(pyrrole) which could be a factor in determining the sensitivity of the sensor. The nature of the affinity molecule and analyte may also contribute to the sensor signal. That is the physical size of the analyte and the magnitude of the induced changes in the affinity molecule will all contribute to the observed response.

Preferably the conducting polymer used should permit immobilisation of the affinity molecule during the electropolymerisation process. This provides intermittent contact between the polymer film and bio-affinity molecule which may influence the magnitude of the response. Thus poly(pyrrole) is preferred because electropolymerisation can be achieved under neutral aqueous conditions thus permitting the entrapment of the affinity molecule during polymer deposition. The polymerisation of 3-methylthiophene, however, has to be performed in acidic non-aqueous conditions which compromises bio-affinity molecule stability. Thus, the immobilisation of the bio-affinity molecule may subsequently be effected by gel entrapment over the preformed conducting polymer film. Therefore, it is believed that the type of conducting polymer used is a compromise between analyte access to the bio-affinity molecule, the intimacy between the conducting polymer film and the bio-affinity molecule, and the properties of the supporting conducting polymer to report analyte interaction.

Therefore the type of conducting polymer used may be expected to depend on the type of bio-affinity molecule/analyte being monitored.

The interrogation technique used is impedance spectroscopy. Measurements made over a wide frequency range (typically 100 kHz–0.01 Hz) make it possible to characterise different interfacial and bulk regions of conducting polymer films. Impedance data can be represented in a number of different forms all of which place a different weighting on parts of the frequency spectrum. Thus, by using an impedance function or parameter it is possible to highlight/amplify changes in conducting polymer behaviour during analyte interaction with immobilised affinity molecule. This is not possible with techniques such as amperometry where the recorded response is a summation of all the electrochemical properties (i.e. the processes cannot be separated). Surface potential (charge) has been measured, but this is probably not a viable selective way of identifying interaction between the analyte and the affinity component, and only charged molecules can be assessed in this way.

Immobilisation of the affinity molecule is preferably achieved by entrapment within the conducting polymer film during the electropolymerisation process. When this is not permitted due to the conditions required for polymerisation (i.e. acidic organic phase), then the affinity molecule may be adsorbed onto pre-formed conducting polymer film. The adsorbed affinity molecule may then be "fixed" by an overlaying gel-like polymer, notably a hydrogel which allows the inclusion of water for analyte transport and subsequent interaction with the immonbilised affinity molecule. A typical hydrogel would be poly (acrylamide). Covalent coupling of affinity molecule surface lysyl residues to conducting polymer derivatives is also not precluded as an immobilisation technique.

A sensor in accordance with the invention most preferably comprises an interdigitated electrode whereby the conducting polymer layer or film bridges the gap separating the electrode digits. The affinity molecule may be either entrapped within the bridging film or alternatively immobilised on the side of the conducting polymer layer remote from the electrode.

Conducting polymer thickness should be sufficient to bridge the gap between interdigitated electrodes (10 $\mu$m). The effect of film thickness on tie responsiveness of the polymer layer has yet to be conclusively determined, however, conducting polymer films thicker than 5 $\mu$m were found to be unstable and readily detached from the interdigitated electrode surface.

To ensure rapid transfer of solute through the gel layer, gel thickness is preferably less than 50 $\mu$m, but up to 200 $\mu$m is possible. The key consideration is adequate affinity component in contact with the conducting polymer.

The conducting polymer may conveniently be produced by electropolymerisation.

The invention is illustrated by the following non-limiting Examples and FIGS. 1 to 8 of the accompanying drawings which illustrate results of the Examples.

EXAMPLE 1

A sensor was produced (using the procedure below) based on an Interdigitated gold electrode (IDE) (7 mm×7 mm including electrode contact pads, 10 $\mu$m thick digits, 15 $\mu$m separation, total of 50 digits with 25 connected to one pad and 25 connected to the other pad) and incorporating an immobilised layer of L(+)-lactic dehydrogenase (LDH) to represent a model system. LDH catalyses the reversible reduction of pyruvate with NADH cofactor acting as the electron donor.

Poly(3-methylthiophene) was deposited onto the IDE via electropolymerisation from a degassed acetonitrile solution containing 0.1M $HClO_4$ and 0.1M 3-methylthiophene. Electropolymerisation was achieved through potential scanning between −0.4–1.5V (vs SCE) at a scan rate of 100 mV/s.

LDH (250 Units) was adsorbed onto the surface of the poly(3-methylthiophene) coated IDE. 5 $\mu$l acrylamide/bis-acrylamide (10% w/v) containing 1 $\mu$l TMED was then applied to the surface of the coated IDE. Polymerisation of acrylamide/bis-acrylamide was achieved through the addition of 5 $\mu$l ammonium persulphate (10% w/v). The polymerisation process is complete within 2 min and results in a strongly adherent film.

The resultant sensor was then subjected to a number of tests.

Figure 1:
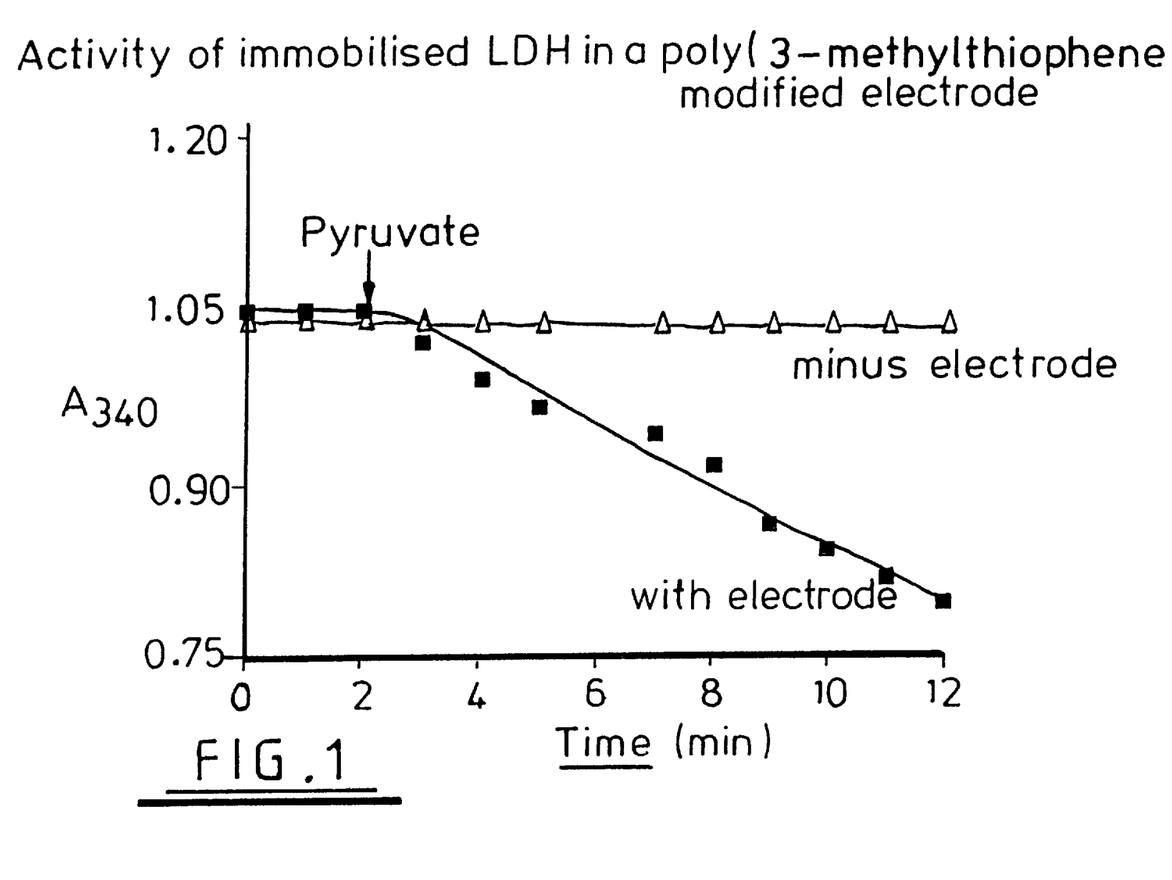
FIG. 1 depicts the activity of an immobolised enzyme versus time for a first exemplary sensor embodiment.

In order to demonstrate that the LDH had not been denatured during the immobilisation process UV spectroscopy was used to measure the enzyme activity of the sensor. The assay consisted of phosphate buffer (pH 6, 50 mM) containing 1 mM NADH. The IDE was submerged in the reaction mix and the reaction initiated by the addition of 5 mM sodium pyruvate. NADH oxidation was recorded at 340 nm. A control experiment was conducted without the electrode present in the reaction mix. The results are shown in FIG. 1 which clearly demonstrates that the immobilised enzyme maintained its activity as witnessed by the reduction in absorbance by NADH with time.

Various impedance measurements were performed using a Voltech frequency response analyser connected to a PARC 273 potentiostat. Measurements were performed in phosphate buffer (pH 6, 50 mM containing 50 mM KCl) previously deoxygenated by $N_2$. The impedance of the enzyme IDE electrode was measured from a starting frequency of 1 Hz and ended at 100,000 Hz at an amplitude of 20 mV. Raw data obtained from the frequency response analyser were presented as a output voltage:input voltage ratio which was used to calculate the real part ($Z_r$) and imaginary part ($Z_{im}$) of the impedance from which the total impedance (IZI) was derived.

Exposure of the modified IDE to pyruvate caused a decrease in the ratio (thus impedance) indicating an increase in conductivity particularly in the low frequency region. A plot of $Z_{im}$ vs frequency of the same data resulted in a dispersion/relaxation (i.e. peak) at a particular frequency and that frequency was used to extract the impedance. That frequency was chosen because dispersions/relaxations are indicative of specific processes occurring within the conducting polymer.

Figure 2:
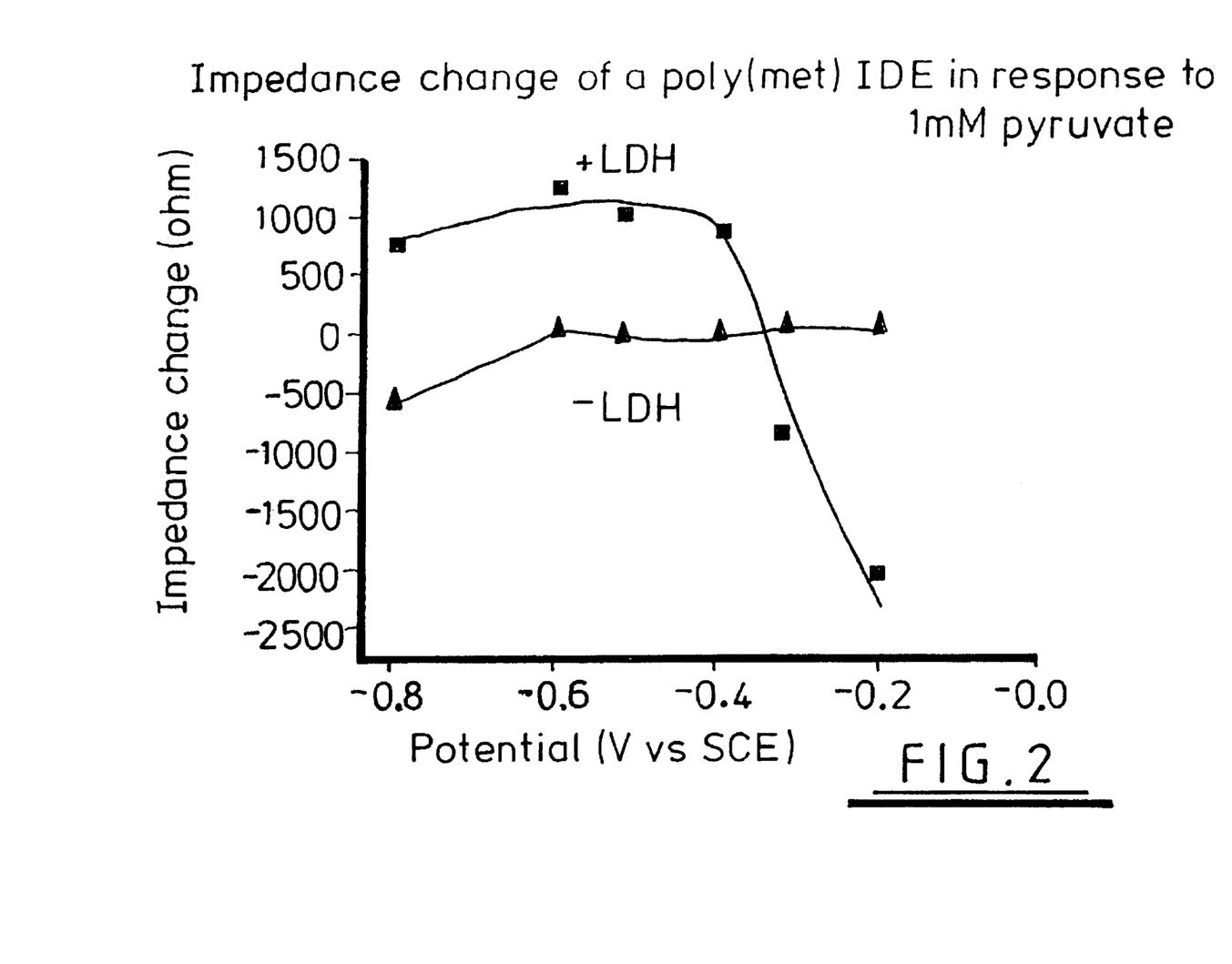
FIG. 2 depicts an impedance change versus applied voltage response to pyruvate for the first exemplary sensor.

FIG. 2 illustrates the effect of bias potential on the response of the sensol to pyruvate. Measurements were performed in saline phosphate buffer (pH 6, 50 mM containing 50 mM KCl). The impedance of the modified IDE was allowed to attain steady state at each potential and the response to 1 mM sodium pyruvate recorded. At potentials more positive than −0.4 V (vs SCE) a decrease in polymer impedance (resistance) was observed (FIG. 2) but below at more negative potentials the polymer became less conductive following the addition of pyruvate. Use of −0.4V (vs SCE), however, gave the best resolution of impedance plots. A modified IDE containing no enzyme showed relatively negligible impedance changes (FIG. 2) across the same potential range. Thus FIG. 2 shows that the conductivity of the polymer can be modulated by altering the applied bias potential.

The magnitude of the impedance change was also affected by the pH of the bathing solution with an optimum response being observed at pH 5.5.

Figure 3:
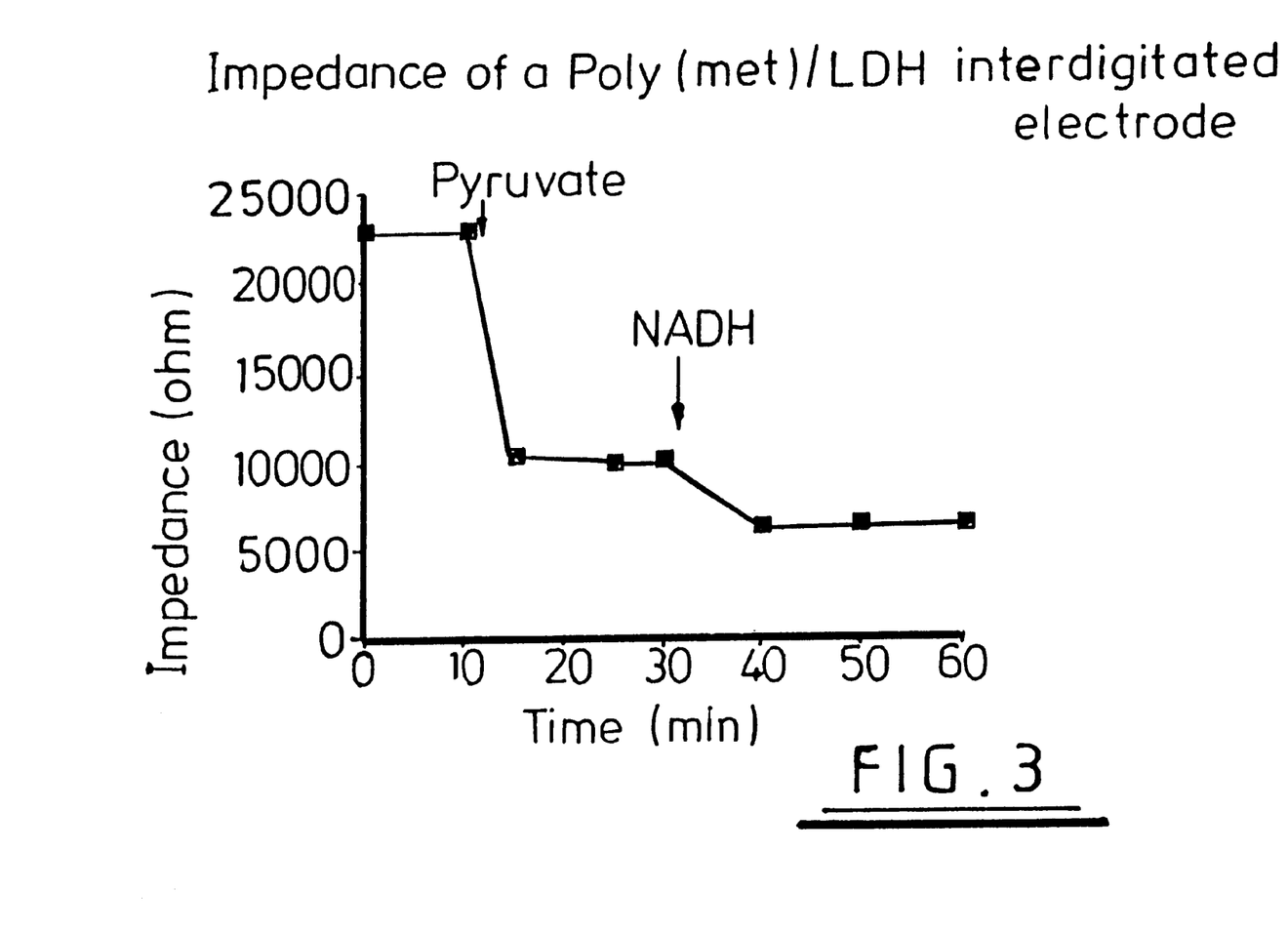
FIG. 3 depicts impedance versus time for the first exemplary sensor in response to pyruvate and then NADH.

FIG. 3 illustrates the dynamic response of a modified IDE to pyruvate (1 mM) and NADH (0.25 mM). Following the addition of pyruvate a rapid drop in polymer impedance was found which attained a steady state value (FIG. 3). This suggests that pyruvate binding to immobilised LDH is an equilibrium process. The addition of NADH co-factor caused a further impedance drop which could be due to polymer oxidation via $NAD^+$ (formed during the course of the enzyme reaction).

Figure 4:
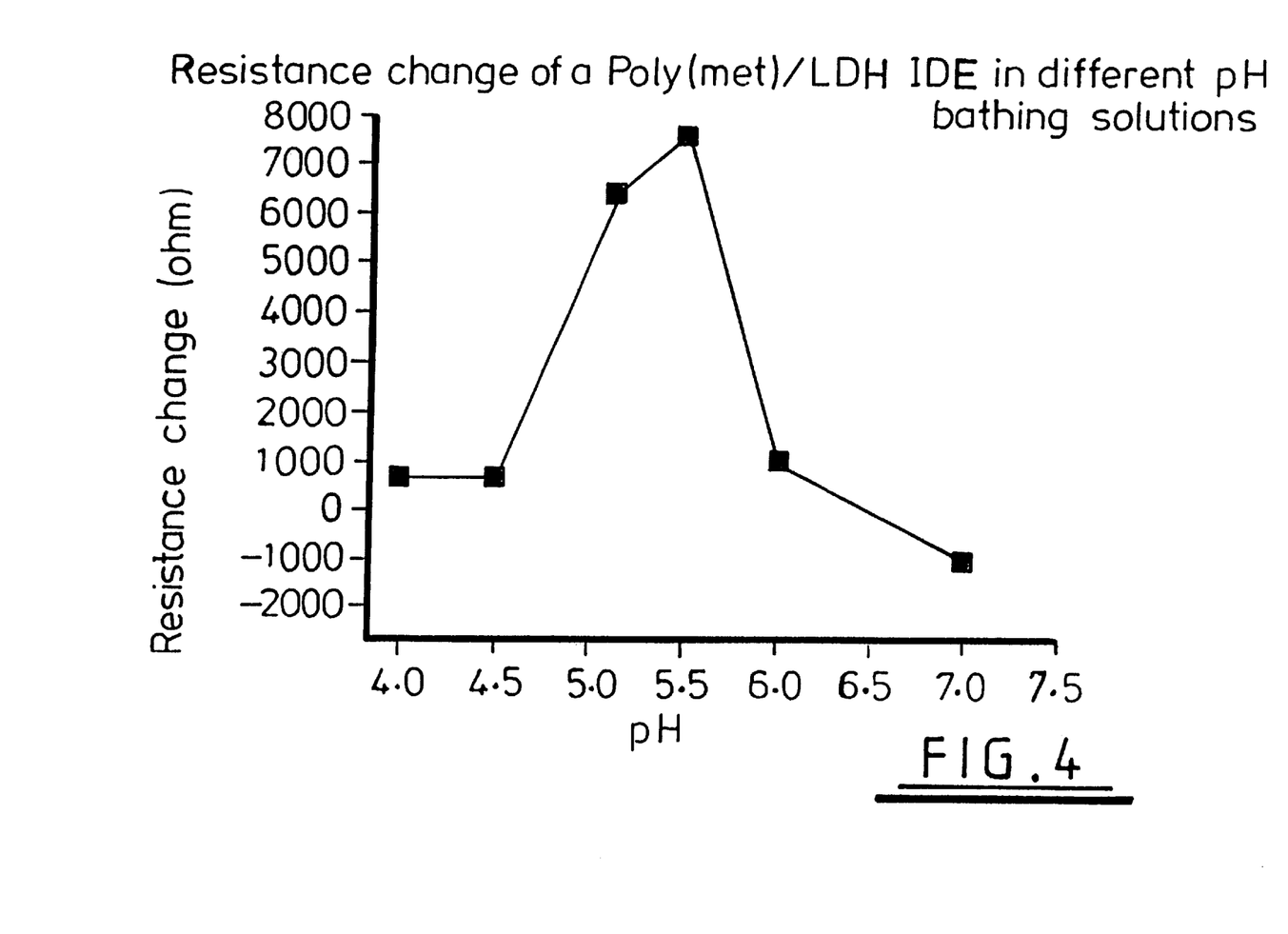
FIG. 4 depicts the exemplary first sensors resistance versus pH.
Figure 5:
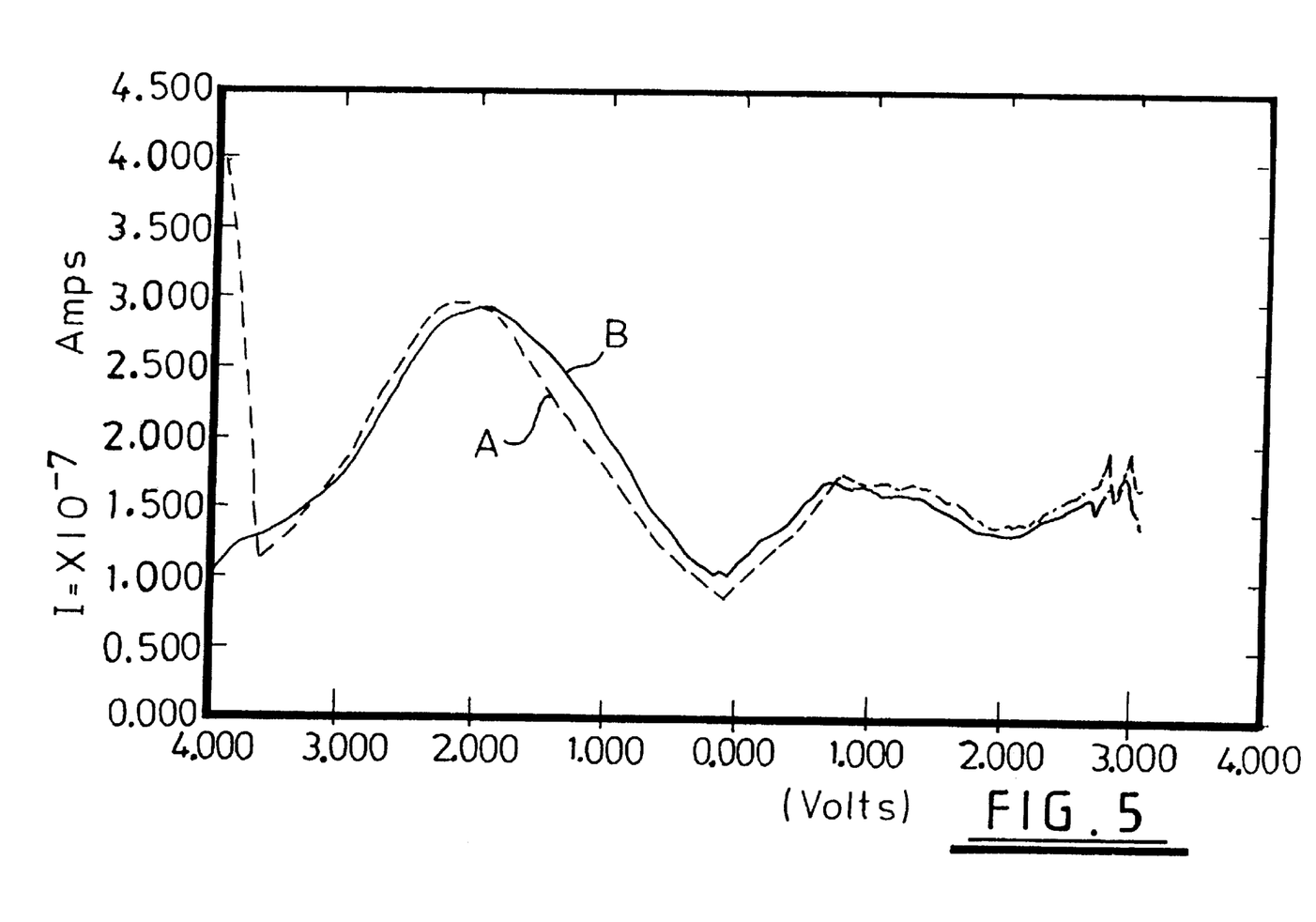
FIG. 5 depicts the exemplary first sensor's current versus voltage response in the presence and absence of pyruvate.

FIG. 4 illustrates the dependence of resistance change on pH for a poly(met)/LDH interdigitated electrode.

Square wave voltammograms (FIG. 5) of the sensor in the presence (A) and absence of (B) pyruvate (1 mM) in saline phosphate buffer demonstrates that the impedance change was a non-Faradaic process (i.e. there was no increase in the peak current recorded in the presence of pyruvate). This removes the possibility of direct electron transfer from the redox centre of LDH to the supporting conducting polymer. In the absence of a Faradaic reaction it is plausible to suggest that the observed changes in polymer impedance during the interaction of pyruvate with immobilised LDH may be due to re-orientation of the conducting polymer chains. It still remains unclear as to how enzyme immobilised on the polymer surface can affect the bulk conducting polymer properties.

The type of immobilisation gel used has had an effect on the pyruvate response of the sensor. When polyacrylamide was replaced with the thermoset gel, poly(vinyl alcohol), an impedance increase was observed (as opposed to an impedance decrease as found when using poly(arylamide). The reason for this significant alteration in response remains unclear but it is most probably that the interaction with the conducting polymer film will be different for poly(acrylamide) and poly(vinyl alcohol). That is to say the interaction of gel phase with the conducting polymer influences the nature of the interaction with the bio-affinity molecule. A problem associated with the use of poly(vinyl alcohol) as the gel phase is one of stability whereby the gel layer detaches from the IDE coated electrode after a prolonged exposure in aqueous solution. In this respect poly(acrylamide) is the preferred choice of hydrogel.

EXAMPLE 2

Figure 6:
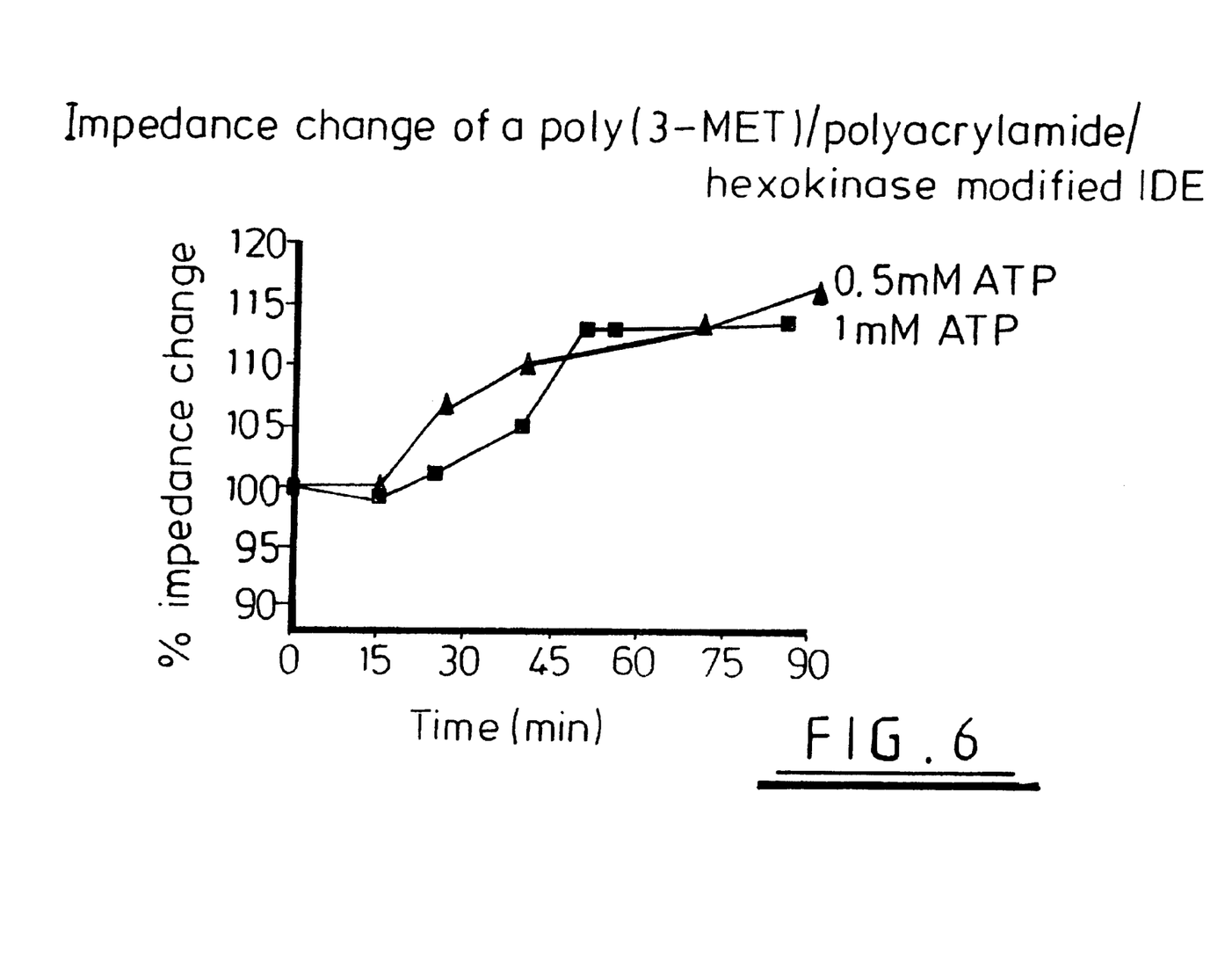
FIG. 6 depicts the impedance change versus time for a second exemplary sensor embodiment in response to ATP.

A further example of a class of enzyme that can find utility in the described sensor is given by work performed using hexokinase. Hexokinase catalyses the phosphorylation of glucose by ATP. The same sensor format was used as previously described save in this case 250 units of hexokinase replaced LDH. FIG. 6 illustrates the response to ATP of a poly(3-methylthiophene) coated electrode containing immobilised hexokinase. It can be seen that the addition of ATP resulted in an impedance (resistance) increase in (as opposed to a decrease in the case of pyruvate/LDH interaction). Saturation of the enzyme sites appears to occur at very low ATP (below 0.05 mM) concentrations which could be due to the affinity constants of the enzyme to ATP substrate. The different response between the pyruvate/LDH and ATP/hexokinase could be attributed to several factors. For example, different enzymes may undergo alternate re-orientation effects.

The LDH and hexokinase model systems demonstrate that the sensor format described may be used to detect further analytes with use of the appropriate enzyme.

EXAMPLE 3

A reagentless immunosensor for leutenising hormone (fertility hormone) has been demonstrated using a similar sensor format. That is measuring the impedance changes of a conducting polymer (containing antibody to leutenising hormone) bridging an IDE. The important difference in this example is that it was possible to record a response using antibody entrapped in poly(pyrrole). By using poly(pyrrole) the entrapment of antibody during polymer deposition was possible by virtue that the polymerisation process could be performed under neutral aqueous conditions which is compatible to antibody stability. In the case of the leutenising hormone sensor the overlaying gel phase would not be expected to restrict diffusion of the leutenising hormone antigen to the immobilised antibody.

Figure 7:
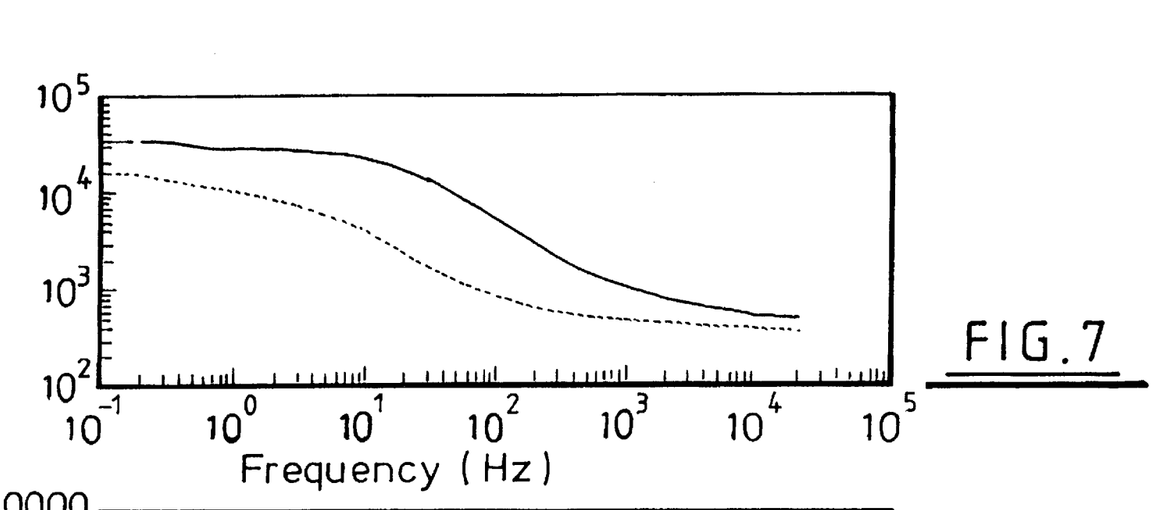
FIGS. 7 and 8 respectively depict the real and imaginary components of impedance versus frequency of applied voltage for a third exemplary sensor embodiment.
Figure 8:
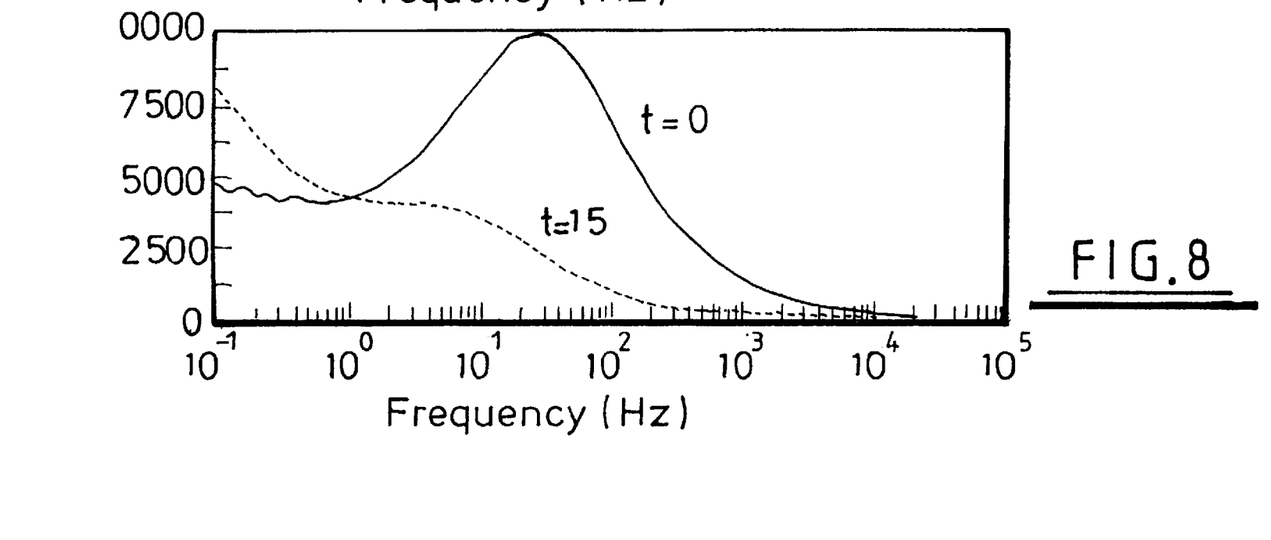

Upon exposure of the sensor to leutenising hormone antigen changes in the impedance properties of the supporting poly(pyrrole) polymer were recorded. Those changes are represented in FIGS. 7 and 8. FIG. 7 showing the real component of the impedance across a range of frequencies before exposure (t=0) and 15 minutes after exposure (t=15), and FIG. 8 showing the imaginary component in the same circumstances. It will be seen that there is a pronounced peak in the imaginary component in the frequency range of from 10 Hz to 100 Hz before exposure, the peak disappearing after exposure. Accordingly measurements will be made at a frequency or frequencies within this range to maximise the sensitivity of the system. The exact frequency selected may be selected to maximise the change that occurs between the measurements before and after exposure.

Thus FIG. 8 shows that changes in the polymer will be highlighted by changes in the magnitude and position of the peak (which may be referred to as the relaxation point). Although larger responses can be obtained at frequencies to either side of this relaxation peak those responses result at least in part from processes not dependent upon interactions with the affinity component associated with the conducting polymer. The overall sensor structure can be considered as being made up of a series of layers which exhibit different electrical characteristics. A first layer corresponds to the solution:polymer interface and the impedance of that first layer is a function of the mobility of ions moving in and out of the polymer. This process is typically capacitive in nature. A second layer is the polymer itself, the electrical characteristics of which are of prime interest. A third layer is the electrode:polymer interface the impedance characteristics of which depend upon processes including the transfer of electrons between the polymer and the electrode. This is a predominantly resistive process. Using an interdigitated electrode format minimises the polymer:solution interface contribution. In the illustrated example, processes taking place in the polymer can be identified by reference to a middle frequency range. Looking at a lower frequency would detect substantial contributions from changes in the solution resulting for example from the introduction of analyte. It should be pointed out however that an even more extended frequency range than that shown in FIGS. 7 and 8 could be applied to identify other peaks relating to polymer processes.

It will be noted that the real component of impedance in the example represented in FIG. 7 does not exhibit any frequency-dependent peaks. Accordingly in this example it is sensible to concentrate attention of the imaginary component of the impedance. In other examples however peaks may occur in the real component of the impedance, and in such examples measurements will be made of the real rather than the imaginary component of the impedance.

Sensors in accordance with the present invention are in effect "tuned" to exhibit high sensitivity given the nature of the polymer, the affinity component and the analyte. A sensor may be pre-tuned to exhibit maximum sensitivity to a particular analyte such that a signal is applied to the polymer at a fixed and predetermined frequency and measurements are always made at that frequency. Alternatively, a sensor in accordance with the invention could be "self-tuning", that is software would be provided to apply a wide range of frequencies to the polymer, to record changes in the real and imaginary components of the impedance over time after the sensor is exposed to the analyte, and to analyse data recorded at frequencies corresponding to peaks in the relationship between frequency and measured impedance. The resultant data could then be compared with a database of information representing the response of the sensor to exposure to known analytes with a view to identifying an unknown analyte.

What is claimed is:

1. A sensor comprising:

an immobilised affinity component capable of interacting with a predetermined analyte species and being associated with a conducting polymer such that interaction of the affinity component and the analyte induces a change in electrical properties of the polymer, means for applying an AC signal to the polymer, and means for detecting the response of the polymer to the applied signal to detect the induced change, wherein the detecting means comprises means for measuring the impedance of the polymer at a frequency selected to correspond to a peak in the relationship between frequency and impedance change for the polymer and the predetermined analyte.

2. A sensor as in claim 1, wherein the imaginary component of impedance is measured at a frequency at which there is a peak in the relationship between the imaginary component and frequency.

3. A sensor as in claim 1 wherein the real component of impedance is measured at a frequency at which there is a peak in the relationship between the real component and frequency.

4. A sensor as in claim 1 wherein the polymer is in the form of a layer bridging two electrodes between which the impedance is measured.

5. A sensor as in claim 4, wherein the two electrodes together define an interdigitated electrode assembly.

6. A sensor as in claim 4, wherein the polymer layer has a thickness of less than 5 $\mu$m.

7. A sensor as in claim 4, wherein the layer of the conducting polymer contains, or incorporates a layer of, immobilised affinity component.

8. A sensor as in claim 7, wherein the affinity component is entrapped within a gel layer provided on the conducting polymer layer on the side thereof remote from the electrodes and the gel thickness is less than 50 $\mu$m.

9. A sensor as in claim 1 wherein the affinity component is immobilised within the conducting polymer.

10. A sensor as in claim 1, wherein the affinity component is immobilised by entrapment in a gel provided on the conducting polymer.

11. A sensor as in claim 1, wherein the conducting polymer is poly(3-methylthiophene).

12. A sensor as in claim 1 wherein the affinity component is a macromolecule.

13. A sensor as in claim 1 wherein the affinity component is a biocomponent.

14. A sensor as in claim 13, wherein the biocomponent is an enzyme.

15. A sensor as in claim 14, wherein the enzyme is a kinase or dehydrogenase, or L(+) lactic dehydrogenase suitable for measuring pyruvate.

16. A sensor as in claim 15, wherein the conducting polymer is a poly(pyrrole).

17. A sensor as in claim 13, wherein the affinity component is an antibody, antigen, lectin or receptor.

18. A method for enhancing the sensitivity of a sensor said method comprising:

associating an immobilised affinity component capable of interacting with an analyte species with a conducting polymer such that the interaction of the affinity component and the analyte induces a change in the electrical properties of the polymer, applying AC signals to the polymer, and detecting a response of the polymer to the applied signals to detect the induced change, wherein the impedance of the polymer is measured over a wide frequency range, at last one peak in the relationship between frequency and impedance change resulting from exposure of the polymer to the analyte is detected, and the sensor is operated at a frequency or frequencies corresponding to a detected peak or peaks.

* * * * *